United States Patent [19]
Farzin-Nia

[11] Patent Number: 5,295,823
[45] Date of Patent: Mar. 22, 1994

[54] ORTHODONTIC APPLIANCES HAVING IMPROVED BONDING CHARACTERISTICS

[75] Inventor: Farrokh Farzin-Nia, Inglewood, Calif.

[73] Assignee: Ormco Corporation, Glendora, Calif.

[21] Appl. No.: 969,410

[22] Filed: Oct. 30, 1992

[51] Int. Cl.$^5$ .............................................. A61C 3/00
[52] U.S. Cl. ...................................................... 433/9
[58] Field of Search ............................. 433/8, 9, 217.1

[56] References Cited

U.S. PATENT DOCUMENTS

| | | |
|---|---|---|
| 4,068,379 | 1/1978 | Miller et al. |
| 4,165,561 | 8/1979 | Miller et al. |
| 4,243,386 | 1/1981 | Kawaguchi ........................ 433/9 |
| 4,430,061 | 2/1984 | Webb et al. ........................ 433/9 |
| 4,460,336 | 7/1984 | Smith et al. ........................ 433/9 |
| 4,681,538 | 7/1987 | DeLuca et al. ........................ 433/9 |
| 4,752,221 | 6/1988 | Hanson et al. ........................ 433/9 |
| 4,838,786 | 6/1989 | Reher et al. ........................ 433/9 |
| 4,927,361 | 5/1990 | Smith et al. ........................ 433/9 |
| 5,071,344 | 12/1991 | Wong et al. ........................ 433/9 |
| 5,108,285 | 4/1992 | Tuneberg ........................ 433/9 |

FOREIGN PATENT DOCUMENTS 2563426 10/1985 France ........................ 433/9

OTHER PUBLICATIONS

Metal Handbook, J. H. Clare et al., "Metallic Coating Processes—Thermal Spray Coatings", pp. 361-374, vol. 5, 9th Ed.

Precision Metal Magazine, P. Sioshansi, "Surface Engineering by Ion Implantation", Dec., 1988.

Spire Corporation brochure "Iongaurd ™ 2000 Bearing And Gear Surface Treatment".

Machine Design, P. Sioshansi, "Surface Modification by Ion Implantation", Mar. 20, 1986.

Spire Corporation brochure "Ionguard ™ Surface Treatment".

Primary Examiner—Gene Mancene
Assistant Examiner—Cindy A. Cherichetti
Attorney, Agent, or Firm—Wood, Herron & Evans

[57] ABSTRACT

Orthodontic appliances having improved bonding characteristics and methods of making such orthodontic appliances are disclosed. The appliances to which the present invention is applicable have a metal bonding base and tooth contact surface. Primary mechanical interlock retention means or surface is applied to the tooth contact surfaces. The primary retention surface may be 1) a mesh, 2) a layer of metallic or non-metallic particles (such as spheres, rods, shards, etc.), or 3) grooves, including undercuts, formed in the tooth contact surface. The appliances preferably further comprise secondary mechanical bond strength enhancement means or treatment. Suitable secondary enhancement treatments include 1) surface roughening (e.g., ion bombardment or other etching processes), 2) particles on the order of 5-200μ flame spray coated on the primary retention surface, and 3) a chemically activatable material, such as SiO$_2$ deposited on the primary retention surface. Chemical activation may also be used to activate the chemically activatable material, such as silanation of SiO$_2$.

21 Claims, 3 Drawing Sheets

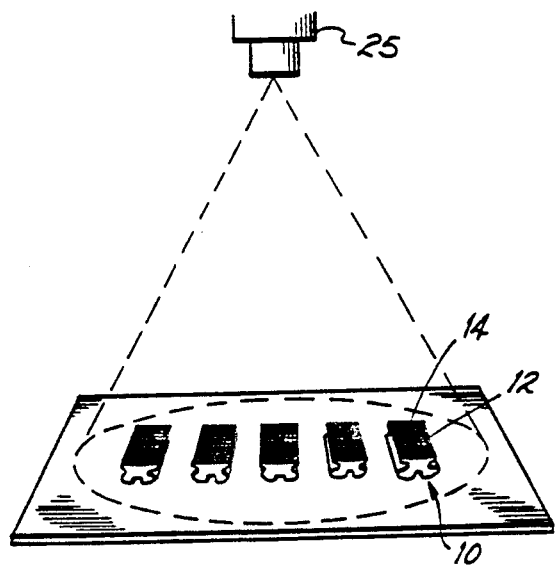 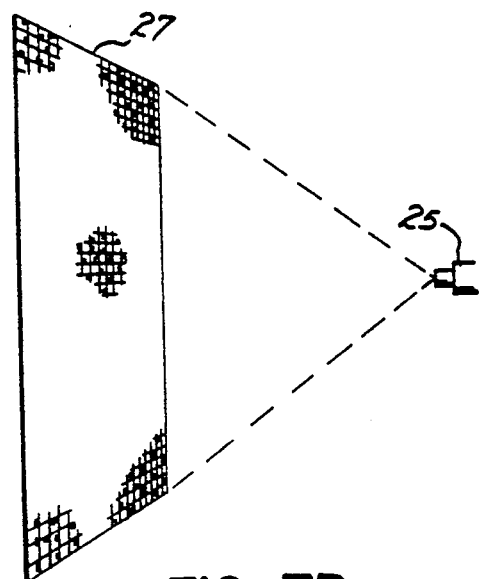
FIG. 7A  FIG. 7B
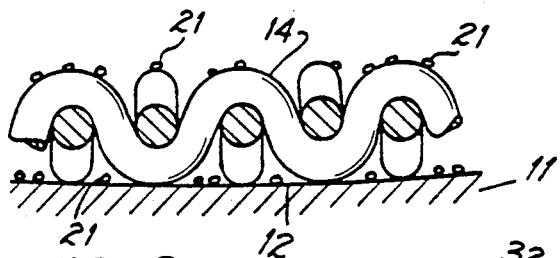
FIG. 8
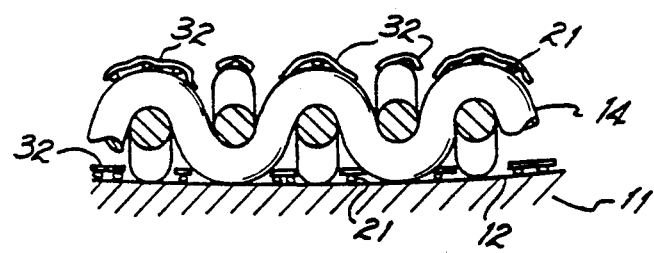
FIG. 9
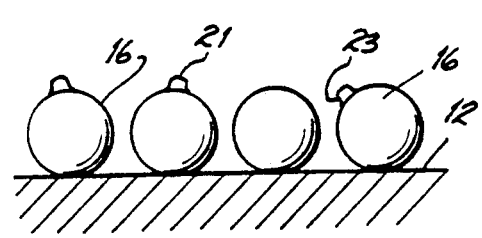 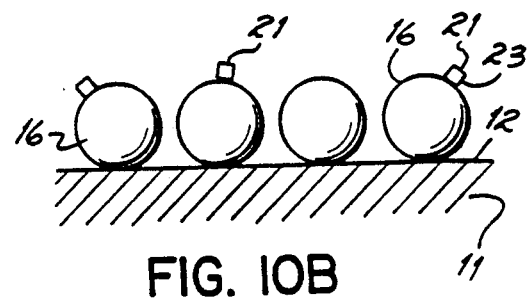
FIG. 10A  FIG. 10B 5,295,823

ORTHODONTIC APPLIANCES HAVING IMPROVED BONDING CHARACTERISTICS

FIELD OF THE INVENTION

This invention relates to orthodontic appliances having improved bonding characteristics designed for attachment directly to the teeth of a patient and methods of making such appliances.

BACKGROUND OF THE INVENTION

In the practice of orthodontics, orthodontic appliances such as brackets are typically secured directly to teeth using an adhesive bonding system. In the course of most orthodontic procedures, forces are applied to the orthodontic brackets by orthodontic archwires, which cause maloccluded teeth to move in a predetermined fashion. Thus, the bonding of orthodontic appliances to teeth is of critical importance for several reasons: 1) to ensure proper transfer of the forces directly to the teeth; 2) to ensure that no undue forces are exerted on the teeth, particularly during removal of the appliances, which may cause removal of enamel; and 3) to ensure that the appliances are not unintentionally debonded prior to the completion of the treatment.

With respect to orthodontic brackets having a metal bonding surface, various solutions have been suggested in the prior art to provide or enhance the bonding characteristics of the appliance. For example, U.S. Pat. Nos. 4,165,561 and 4,068,379 disclose the use of a metal mesh welded to the bonding base of the appliance in order to provide acceptable mechanical bonding characteristics. U.S. Pat. No. 4,927,361 suggests the use of particles in order to provide a porous structure on the tooth contact surface of the appliance. However, these types of brackets are made of materials which are substantially non-chemically reactive, and thus are limited with respect to the bond strengths that can be obtained since they rely on the mechanical bonding characteristics of the bracket.

With respect to non-metal brackets, e.g., brackets made of a ceramic material, bonding of the brackets generally incorporates the use of a chemical treatment so that high bond strengths between bracket and tooth are obtained. However, use of chemically reactive bonding adhesives generally requires special handling and care in order to obtain desired bonding strengths, as set forth in U.S. Pat. No. 4,681,538. Additionally, due to the high bond strengths obtained with ceramic-type brackets, and the manner in which the bonds are fractured, a much higher risk is presented that enamel may be removed from the tooth during bracket removal.

The present invention is intended to overcome the various drawbacks discussed above with respect to bonding brackets to teeth and encompasses improved orthodontic appliances and methods of making such appliances which result in improved bonding characteristics without presenting any substantially increased risk of removing enamel from the tooth.

SUMMARY OF THE INVENTION

The invention, in its broadest context, contemplates providing an orthodontic appliance (such as a bracket) having a metallic bonding base and tooth contact surface with the combination of a) primary mechanical interlock retention means, including undercut regions, which has the capability of providing adequate bond strength when adhered to a tooth enamel surface using a dental adhesive, and b) secondary mechanical bond strength enhancement means applied to the primary retention means. Generally speaking, the minimum shear bond strength that is considered adequate for metal brackets, as tested on brackets adhered to yearling bovine enamel tooth surfaces, is approximately 6.0 kilograms of the load. This figure is dependent upon several variables, including adhesive type, particular bracket base material, and enamel surface preparation, among other things.

In a preferred embodiment, the undercut regions of the primary mechanical interlock retention means, which facilitate mechanical bonding of the appliance to a tooth enamel surface using a dental adhesive, are provided by a) bonding particles to the bracket base such as metal or ceramic spheres, shards, rods, cubes, or the like, which in combination with the base provide the undercut regions; b) a mesh bonded to the tooth contact surface, the strands of which provide the undercut regions; or, alternatively, c) forming undercut regions, including grooves, in the tooth contact surface. The primary mechanical interlock retention means can be provided in accordance with the teachings of one or more of the following U.S. Pat. Nos.: 5,108,285, 5,071,344, 4,927,361, 4,838,786, 4,752,221, 4,460,336, 4,165,561 and 4,068,379.

The secondary mechanical bond strength enhancement means applied to the primary retention means serves to provide additional undercut regions to enhance mechanical bonding of the appliance to a tooth enamel surface using a dental adhesive and/or to increase the surface area of the primary retention means to enhance the mechanical bonding of the appliance to a tooth enamel surface. Increasing the surface area of the primary retention means may be accomplished by surface etching or roughening or by adhering particles to the primary retention means. If etching is used, preferably it is accomplished by ion beam bombardment. If particles are adhered to the primary retention means to increase its surface area, the particles can be of any suitable material and may be bonded in any suitable manner, such as metallic cubes sintered to the strands of a metallic mesh primary retention means. Increasing the undercut regions of the primary retention means may be accomplished by sintering metallic spheres to the strands of a metallic mesh. The metal spheres, since they themselves provide undercut regions, augment the undercut spaces provided by the primary retention means (e.g., metal mesh). Additionally, the spheres provide increased surface area, further augmenting or enhancing the mechanical bond strength when the bracket is adhered to a tooth enamel surface using a dental adhesive.

In addition to increasing the surface area of the primary retention means or increasing the undercut of the primary retention means, the secondary mechanical bond strength enhancement means may be accomplished by depositing a chemically activatable material on the primary retention means. The chemically activatable material may be deposited in a continuous or intermittent layer on the primary retention means, or it may be applied in the form of particles of a chemically activatable material. In the case of particles, one preferred deposition method is Diamond Jet Coating of ARMACOR M powder of approximately −400 mesh. The use of such particles further enhances the bond strength of the appliance by increasing the surface area of the primary retention surface. Finally, chemical activation of the chemically activatable material may be employed to further enhance the bond strength of the appliance by providing additional bonding sites.

From the foregoing, it is apparent that certain of the secondary mechanical bond strength enhancement treatments applied to the primary mechanical interlock retention surface can augment the strength of the bond between the tooth and appliance provided by the primary retention surface in two distinct manners. For example, a secondary treatment of metal spheres or particles enhances the mechanical bond strength of the primary surface, such as a metal mesh, by providing both added surface area and additional undercut spaces. Similarly, a secondary treatment of chemically activatable particles such as particles which include or contain silicon dioxide ($SiO_2$) can increase the surface area and, when chemically activated, as by silanation, can increase the number of surface bond sites.

The present invention further encompasses methods of improving the bonding characteristics of an orthodontic appliance, preferably having a metallic bonding base and tooth contact surface. The methods generally comprise applying the primary mechanical interlock retention means on the tooth contact surface of the appliance and thereafter applying secondary mechanical bond strength enhancement means to the primary retention means.

As discussed above with respect to the orthodontic appliances, the primary mechanical interlock retention means application step may comprise a) adhering particles to the tooth contact surface, b) bonding a mesh to the tooth contact surface, or c) forming undercut regions, including grooves, in the tooth contact surface. As will be appreciated, each of the above primary retention means includes undercut regions which facilitate adequate mechanical bonding of the appliance to a tooth enamel surface using a dental adhesive. The subsequent secondary mechanical bond strength enhancement means application step is preferably selected from a) surface etching to increase the surface area of the primary retention surface, b) adhering particles to the primary retention surface, and c) depositing a chemically activatable material on the primary retention surface. Additionally, the method may further comprise chemically activating the chemically activatable material deposited on the primary retention surface.

It will be appreciated that in the context of the present invention the term "chemically activatable material" is intended to include any one of many materials which includes an oxide of one of the following elements: silicon, barium, boron, titanium, magnesium, zirconium, potassium, calcium, sodium, and thallium. One particularly suitable material is silicon dioxide ($SiO_2$); however, virtually any glass oxide of the type typically used in glass manufacturing is suitable for use in the context of the present invention.

These and other features and advantages of the present invention will become apparent to persons skilled in the art with reference to the detailed description which follows, taken in combination with the drawings.

BRIEF DESCRIPTION OF THE DRAWINGS

FIG. 7A is a perspective schematic view, similar to FIG. 5, illustrating another aspect of a method of the present invention;

FIG. 7B is a perspective schematic view illustrating an alternative embodiment of a method of the present invention;

FIG. 8 is an exploded cross-sectional view, partially broken away, of an orthodontic appliance of the present invention.

FIG. 9 is an exploded cross-sectional view, partially broken away, of another orthodontic appliance of the present invention.

FIG. 10A is an exploded cross-sectional view, partially broken away, of an alternative orthodontic appliance of the present invention; and FIG. 10B is an exploded cross-sectional view, partially broken away, of yet another alternative orthodontic appliance of the present invention.

DETAILED DESCRIPTION OF THE INVENTION

Figure 1:
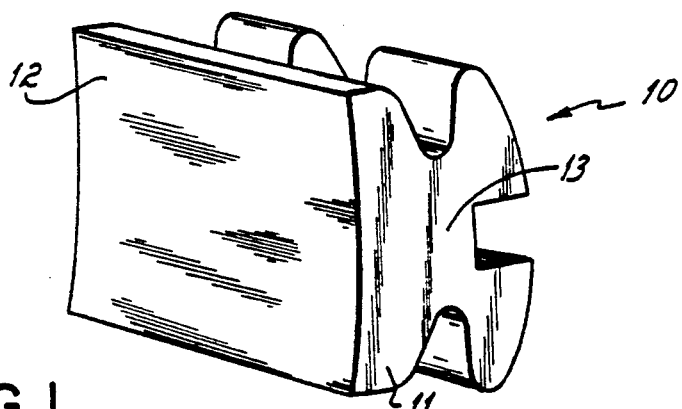
FIG. 1 is a perspective view of an orthodontic appliance made in accordance with one embodiment of the present invention.

Referring to FIG. 1, there is illustrated an orthodontic appliance (bracket) 10 made of a substantially non-chemically reactive material. The phrase "chemically reactive" is used herein to refer to the capability of a material or coating to be activated for adhesion to a dental adhesive when chemically treated, or to have significant chemical adhesion to adhesives as compared to the chemical adhesion of stainless steel, and as a result of this, to form a suitable chemical bond when a dental adhesive is used to bond the tooth contact surface of the bracket to a tooth.

In the particular embodiment illustrated in FIG. 1, orthodontic appliance 10 is an orthodontic bracket made of metal, preferably stainless steel. Orthodontic appliance 10 has a bonding base 11 which has a tooth contact surface 12 designed to be bonded to the exterior surface of a tooth using a suitable dental adhesive. As shown, the bonding base 11 is integrally formed as a part of the orthodontic appliance 10, however it need not be, and is made of stainless steel, or other metallic material. It will be understood that orthodontic appliance 10 may be made of any suitable material, so long as the bonding base 11 and tooth contact surface 12 are substantially chemically non-reactive. The bracket bonding base 11 need not be the same material as the body portion 13 of the bracket, and may, for example, be metallic or non-metallic, such as ceramic.

In accordance with the principles of the present invention, tooth contact surface 12 is provided with a primary mechanical interlock retention means or surface, incorporating undercut regions, spaces or voids, and a secondary mechanical bond strength enhancement means or treatment. The primary retention surface provides adequate mechanical bond strength to enable the bracket to be satisfactorily adhered to a tooth enamel surface using a dental adhesive. The secondary treatment enhances the mechanical bond strength of the bracket.

Primary Mechanical Interlock Retention Means

Figure 2A:
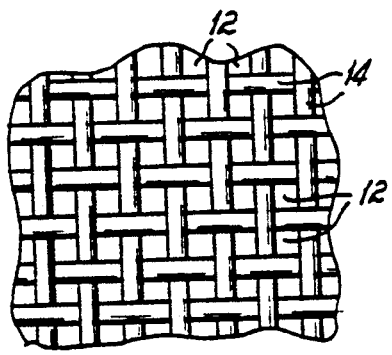
FIG. 2A is an enlarged top plan view, partially broken away, of one embodiment of the present invention.
Figure 2B:
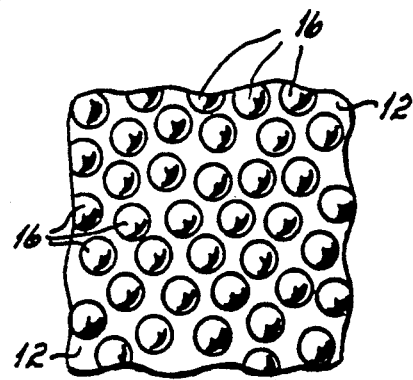
FIG. 2B is an enlarged top plan view of an alternative embodiment of the present invention.
Figure 3A:
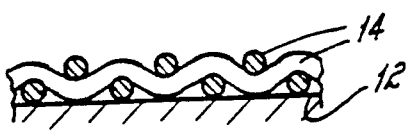
FIG. 3A is a cross-sectional view, partially broken away, of the orthodontic appliance of FIG. 2A.
Figure 3B:
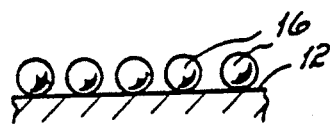
FIG. 3B is a cross-sectional view, partially broken away, of the orthodontic appliance of FIG. 2B.
Figure 2C:
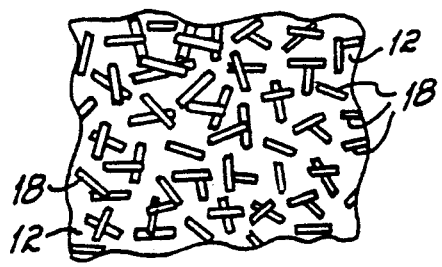
FIG. 2C is an enlarged top plan view of another embodiment of the present invention.
Figure 3C:
FIG. 3C is a cross-sectional view, partially broken away, of the orthodontic appliance of FIG. 2C.
Figure 3D:
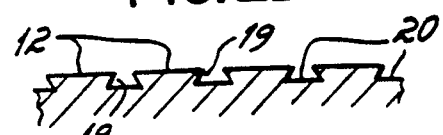
FIG. 3D is a cross-sectional view, partially broken away, of the orthodontic appliance of FIG. 2D.

The bracket 10 is provided with primary mechanical interlock retention means (hereinafter "primary retention surface") incorporating undercut regions or spaces. As shown in FIGS. 2A and 3A, the primary retention surface may comprise a mesh or screen 14 of metal or non-metal secured to tooth contact surface 12, as is well known in the art, by sintering or diffusion bonding Alternatively, other means may be secured to tooth contact surface 12 in order to enhance the mechanical bonding characteristics of the bracket. FIGS. 2B and 3B shows as one alternative a plurality of metallic or ceramic spherical particles or "balls" 16 diffusion bonded in a substantially monolayer fashion on tooth contact surface 12. Preferably, balls of $20\mu$ or greater size are suitable to provide sufficient undercut regions for adequate mechanical bonding, as defined previously. Alternatively, as shown in FIGS. 2C and 3C, a plurality of rod-shaped or irregular particles 18 or shards of any suitable material are diffusion bonded in a random pattern on tooth contact surface 12. Finally, the primary retention surface may comprise a plurality of grooves 20, including undercuts 19, formed (preferably by machining) in the tooth contact surface 12 of bracket 10. It will be appreciated by persons skilled in the art that other primary mechanical retention means may be utilized in the practice of the present invention.

Figure 4:
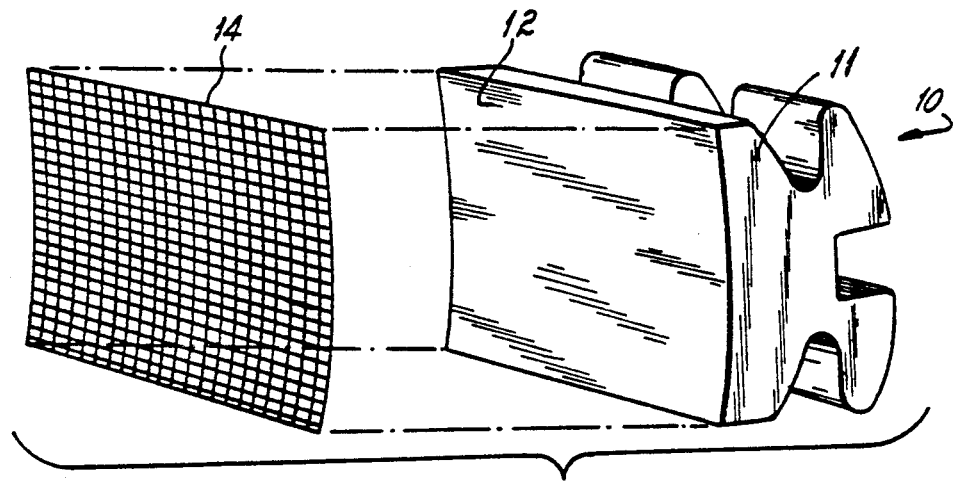
FIG. 4 is an exploded view of one embodiment of an orthodontic appliance of the present invention.

A preferred embodiment of the present invention is illustrated in exploded view in FIG. 4, and includes a mesh 14 made of stainless steel and having a mesh size of $100 \times 100$ openings per inch. It is to be understood that the mesh size and mesh material may be varied as desired. Screen 14 is preferably diffusion bonded to tooth contact surface 12 by procedures well known in the art, such as those described in U.S. Pat. Nos. 4,165,561 and 4,068,379, the contents of which are hereby fully incorporated herein by reference.

Secondary Mechanical Bond Strength Enhancement Means

It has been determined that applying a secondary mechanical bond strength enhancement means or treatment (hereinafter "secondary enhancement treatment") to at least a portion of the primary retention surface will enhance the overall mechanical bond strength characteristics of orthodontic bracket 10 when cemented to a tooth enamel surface. In one preferred form, the secondary treatment comprises increasing the surface area of the primary retention surface by a fine roughening procedure. It will be appreciated that the roughing procedures described below are equally applicable to the bracket 10 regardless of the specific primary retention surface utilized (i.e., mesh, ball base, rods, particles, grooves, etc.).

In a preferred embodiment, the secondary enhancement treatment comprises a roughened surface which is formed by subjecting bracket 10 to a high energy surface treatment. More particularly, after woven mesh 14 has been secured to tooth contact surface 12, bracket 10 is subjected to ion bombardment whereby very small amounts of material are removed from the mesh 14 and the exposed areas of tooth contact surface 12. This procedure increases the roughness of the exposed surfaces and thus the surface area thereof is increased. The increased surface area provides more area for mechanical adhesion with the dental adhesive used to bond the bracket to the tooth and thus results in increased mechanical bond strength.

Figure 5:
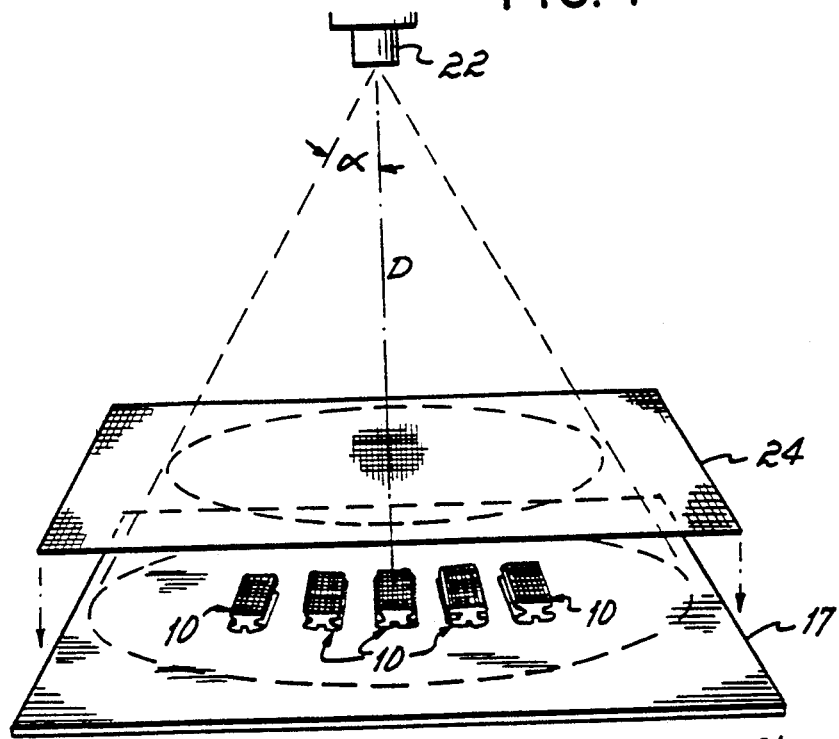
FIG. 5 is a perspective schematic representation of one aspect of a method of the present invention.

In a preferred procedure, depicted schematically in FIG. 5, a plurality of brackets 10 are placed face down (the labial portion of the bracket facing downwardly) on a suitable support structure 17 such that the contact surface 12 and mesh 14 (primary retention surface) are exposed to a high energy source 22 located vertically above the brackets 10 a distance "D". High energy source 22 is activated and directs a stream of high energy ions toward the exposed surfaces of mesh 14 and tooth contact surfaces 12 of brackets 10.

By way of specific example, a plurality of brackets 10 may be subjected to argon ion bombardment from a broad-beam, gridded, Kaufman-type ion source which removes small amounts of material from the exposed surfaces of mesh 14 and tooth contact surfaces 12. This type of ion bombardment or ion beam implantation is a well known procedure to persons skilled in the art which may utilize methods and apparatus commercially available from Spire Corporation of Bedford, Mass.

It has been determined that subjecting only a portion of each bracket 10 to the roughening process is preferred to roughening the entire exposed tooth contact surface 12 and primary retention surface. Thus, selective roughening of tooth contact surface 12 and mesh 14 may be accomplished as schematically shown in FIG. 5 by directing the ion beam through a screen-type mask 24 positioned vertically above the brackets 10 so that only a portion of the exposed surfaces of brackets 10 are subjected to the ion bombardment. To accomplish this, a thin screen 24, preferably made of stainless steel and having a mesh size of $50 \times 50$ openings per inch, is placed above the tooth contact surfaces 12 of the brackets. By selecting the appropriate mesh size of screen 24, the ion bombardment procedure will selectively etch only portions of the bracket. Ideally, screen 24 is selected so that between about 10% and 90% of the surface area of tooth contact surface 12 and mesh 14 are exposed to the ion bombardment, and preferably between about 20% and 50% of those surfaces are exposed.

In the particular embodiment illustrated, about 35% of the surface area of the contact surface 12 and mesh 14 is exposed to ion bombardment. In this preferred embodiment, energy source 22 is located a distance D of about one meter above the brackets 10 and an argon ion concentration of about $1 \times 10^{14}$ ions/cm$^2$ is applied for a time period of about five minutes at a power of 300 watts. As will be appreciated by persons skilled in the art, the ion concentration, type of ion and duration of ion bombardment may be selected to obtain the desired surface roughness for the exposed tooth contact surface 12 and primary retention surface (mesh 14). The distance D which ion source 22 is located above brackets 10 is selected to ensure the desired ion concentration at the bombardment sites. As depicted in FIG. 5, the ions are directed in the form of a beam at the exposed surfaces of brackets 10 at an angle α, which is preferably no greater than about 60 degrees, as measured with respect to a plane perpendicular to tooth contact surfaces 12.

As previously noted, this surface roughening or texturing procedure provides enhanced mechanical bond strength in the form of increased surface area of the primary retention surface (mesh 14) to aid in mechanical bonding of the bracket 10 to a tooth enamel surface using dental adhesive. FIG. 6A shows an enlarged top plan view of a tooth contact surface 12 having a mesh 14 secured thereto, both of which have been subjected to a selective roughening procedure as described above. Tooth contact surface 12 and mesh 14 are thus both provided with regions of surface roughness 26.

It will be appreciated that alternative treatments may be employed to provide the desired surface roughening for increasing the surface area of the primary retention means. For example, chemical etching, bead blasting and shot peening are all believed to be suitable treatments to accomplish the desired roughening, and all are equally applicable regardless of the primary retention surface selected.

Figure 6B:
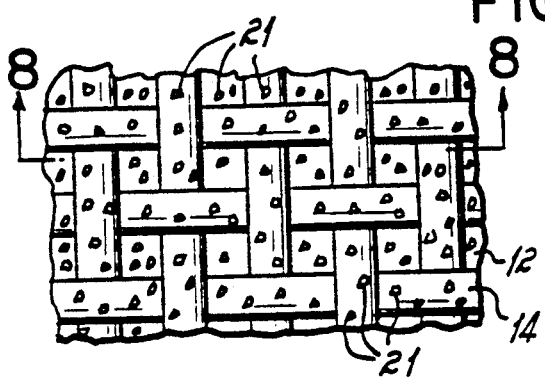
FIG. 6B is an enlarged top view of the tooth contact surface of an orthodontic appliance made in accordance with an alternative embodiment of the present invention.
Figure 6A:
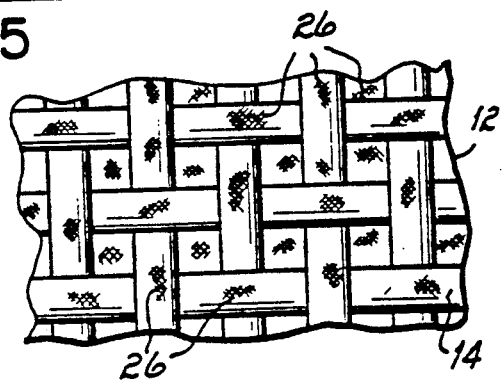
FIG. 6A is an enlarged top view of a tooth contact surface of an orthodontic appliance made in accordance with one embodiment of the present invention.

Referring specifically to FIG. 6B, a portion of an alternative embodiment of an orthodontic bracket made in accordance with the present invention is shown. In this embodiment, the mechanical bond strength characteristics of the metal bracket 10 are improved or enhanced due to the increased surface area provided by bonding small particles 21 to tooth contact surface 12 and mesh 14. Particles ranging in size from about 5μ to about 200μ are preferred. Particles of 400 mesh (less than about 37μ) may also be preferred. Particles 21 are preferably made of a material that permits the particles to be diffusion bonded to contact surface 12 and mesh 14. One suitable material for particles 21 is an alloy sold under the trade name ARMACOR M (−400 mesh), which is an alloy of iron, chromium, silicon and boron, commercially available from Amorphous Technologies International Inc. of Laguna Niguel, Calif. Because the bonding of particles 21 to tooth contact surface 12 and mesh 14 increases the surface area of the primary retention surface (mesh) available for mechanical retention, the overall mechanical bond strength characteristics of the brackets 10 are improved.

Figure 2D:
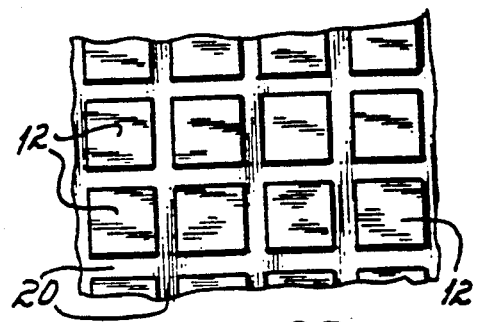
FIG. 2D is an enlarged top plan view of another alternative embodiment of the present invention.

There are several suitable procedures available for bonding particles 21 to tooth contact surface 12 and mesh 14. It should be appreciated that in the alternative embodiments depicted in FIGS. 2B-2D, wherein the primary retention surface is something other than a mesh (i.e., balls, rods, and grooves, respectively), the application of particles 21 to enhance the mechanical bond strength by increasing the surface area is contemplated by the present invention. Thus, the ensuing discussion of bonding particles 21 to a bracket which has a mesh 14 as the primary retention surface is intended solely for purposes of example and is not intended in any way to limit the scope of the present invention.

One preferred method of applying particles 21 to brackets 10 is by thermal spray coating, which is the generic term for a group of well-known and commonly used processes for depositing metallic and non-metallic coatings. These processes include, but are not limited to, flame spray, plasma spray, and HVOF spray, wherein the coating may be sprayed from rod or wire stock, or from powdered material. These types of processes are described in Metals Handbook, J. Clare and D. Crawmer, "Metallic Coating Processes—Thermal Spray Coatings", pp. 361-374, Vol. 5, 9th Ed., the content of which is hereby expressly incorporated herein by reference. In the present invention, which preferably employs powder flame spraying, the particles are melted and ejected from a spray gun 25 at very high speeds against tooth contact surface 12 and mesh 14 in an arrangement shown schematically in FIG. 7A. Alternatively, as shown in FIG. 7B, the powder flame spray is directed against a mesh panel 27 to provide the desired particle coating and subsequently the mesh panel 27 is cut up and adhered to individual brackets in any suitable manner. In the former situation, the particles 21 adhere to both tooth contact surface 12 and screen 14, as shown in FIG. 8, to provide increased surface area, which enhances the mechanical retention and bond strength characteristics of the bracket as a whole. It should be appreciated that FIG. 8 is only intended to be representative of particles 21 adhered to mesh 14 and tooth contact surface 12, and that in actual practice the particle density may be much greater than that shown. In the situation wherein the mesh panel 27 is flame spray coated prior to adherence to individual brackets, the particles 21 will only be adhered to the mesh 14, and not to the tooth contact surface 12 of the brackets 10 (not shown).

In the practice of the present invention, one powder flame spray coating process which may be successfully employed to deposit powder particles on the primary retention surface of a bracket 10 is the Diamond Jet System commercially available from the Boyd Machine & Repair Co., Inc. of Kimmell, Ind. This system utilizes a Type DJ Diamond Jet Gun, model DJA, a model DJC fluid control unit, and a model DJP powder feed unit, all available from METCO (Div. of Perkin-Elmer), Westbury, N.Y., to propel the desired powder particles. In a specific example, wherein 11"×24" mesh panels are spray coated with ARMACOR M (−400 mesh) powder, utilizing the Diamond Jet System, the following parameters may be employed:
 (1) Equipment control settings:
   (a) powder rate: 4.5-5.0 lbs/hr
   (b) propylene fuel: 39-43%
   (c) nitrogen flow: 25 (CFM)
   (d) oxygen ratio: 45%
   (e) air pressure: 50 psi
 (2) Operator parameters:
   (a) total cycle time: 60-70 seconds per panel
   (b) stroke speed: 1.5-2.0 feet per second (along the length of the panel)
   (c) nozzle distance: about 12" from the panel
   (d) number of passes: 4 total (one horizontal, one vertical, two diagonal)

In an alternative particle application method, a thin coating of a tacky adhesive, such as 3M Scotch spray adhesive, is applied over the exposed surfaces of contact surface 12 and the primary retention surface (such as mesh 14). Loose particles of the desired size are sprinkled over the adhesive coating, preferably so that a substantially monolayer of particles has covered the contact surface 12 and mesh screen 14. Thereafter, brackets 10 with the particles adhered thereto are subjected to heating to a temperature of about 1150° C. for about 30 minutes to cause the particles to diffusion bond to tooth contact surface 12 and mesh screen 14. Although in the particular example described, the particles 21 are a metal alloy, such as ARMACOR M (−400 mesh), it will be appreciated that particles 21 may be made of any suitable material, including ceramic, and may or may not be chemically activatable.

FIGS. 10A and 10B show, in an enlarged, schematic cross-section, brackets 10 which have a monolayer of balls 16 as the primary retention surface, and particles 21 applied thereto by flame spray coating and adhesive, respectively, as the secondary enhancement treatment. As shown in FIG. 10A, particles 21 are "slumped" or deformed due to the high temperatures utilized in flame spray coating. Conversely, as shown in FIG. 10B, the particles 21 have substantially retained their original shape (in this case cubic). In either case, the application of particles 21 to the primary retention surface, particularly when that surface comprises mesh 14 or balls 16, results in increased surface area and increased undercuts, such as undercuts 23, both of which enhance the overall mechanical bond strength of the brackets.

In addition to the above-described secondary enhancement treatments (surface etching or roughening and particle application), another alternative secondary treatment contemplated by the present invention is the application of a chemically activatable material (as defined hereinabove) to the primary retention surface of bracket 10 to further enhance the overall bonding characteristics thereof. It will be appreciated that the procedures described hereinafter are applicable directly to brackets having only a primary retention surface, as well as to brackets which have been further treated to include a secondary enhancement treatment such as surface roughening or particle application.

In one embodiment shown in FIG. 9, after surface roughening of mesh 14 and tooth contact surface 12, as described hereinabove, a thin, continuous, uniform layer 32 of a chemically activatable material is deposited over the exposed surfaces of tooth contact surface 12 and mesh 14. To accomplish this, an arrangement generally similar to that shown in FIG. 5 is utilized, but without screen 24 in place. A high-energy source 22 of an appropriate ion is directed to a plurality of brackets 10 supported by support structure 17.

In a preferred embodiment, a thin film of a silicon oxide ($SiO_x$) such as silicon dioxide ($SiO_2$), having a thickness on the order of approximately $2\mu$, is applied to brackets 10 by evaporating high purity silicon dioxide, followed by ionization and impingement on mesh 14 and contact surface 12 of each bracket 10.

By way of specific example, silicon dioxide ions are directed to brackets 10 at 25 Kev and at an ion concentration of about $1 \times 10^{14}$ ions/cm$^2$ for approximately 2 hours. The resultant coating formed by this ion beam implantation process provides a super-adherent, substantially pinhole-free coating 32 over the exposed surfaces of tooth contact surface 12 and mesh 14, as shown in FIG. 9. Application of the silicon dioxide layer 32 by deposition may be performed under vacuum conditions on the order of $1 \times 10^{-7}$ Torr. It is believed that the high energy application of silicon dioxide ions causes the ions to mix with the surface atoms of the mesh 14 and contact surface 12 to form an extremely high-strength bond therewith. This high energy surface treatment provides a thin, uniform coating which does not substantially affect or interfere with any secondary enhancement treatment that may have been previously applied, whether it is adhered particles 21 or roughened regions 26. Thus, the overall bond strength characteristics of brackets 10 are further enhanced since the silicon dioxide layer is capable of chemically bonding with various dental adhesives, and the primary retention surfaces and other secondary enhancement treatment, if utilized, mechanically bond with the adhesive to form high strength, substantially uniform bonds.

It will be appreciated that the present invention, including methods and the orthodontic appliances so made, contemplates application of a chemically activatable layer, such as silicon dioxide, directly onto the primary retention surface or, as described above, onto a primary retention surface to which a secondary enhancement treatment has already been applied.

Subsequent to application of a chemically activatable material, the brackets may be subjected to a suitable treatment which chemically activates the chemically activatable material. For example, silicon dioxide layer 32 may be subsequently activated by treatment with silane to further increase its chemical bonding characteristics and to further improve the overall bond strength of bracket 10. This silane activation, which serves to create chemical bonding sites, is preferably accomplished by immersion of the brackets in a silane solution (composition given below) heated to about 50°±5° C., for about 20 minutes (with periodic stirring). Thereafter, the brackets are sequentially washed with a 10% (by weight) isopropanol solution and de-ionized water. Finally, the brackets are dried in a forced draft oven at 110° C. A suitable silane solution has the following composition:

| Component (source) | Approximate Wt. % |
| --- | --- |
| gamma-methacryloxy-propyltrimethoxy silane (Petrarch Silicones) | 3% |
| glacial acetic acid | 3% |
| de-ionized water | 2% |
| isopropyl alcohol | balance |

Alternatively, tooth contact surface 12, the primary retention surface, and/or the secondary enhancement treatment may be treated directly with silane without any silicon dioxide deposition. This direct silane treatment activates the exposed surfaces, to the extent they are activatable, to provide chemical bonding between the bracket 10 and the dental adhesive used to adhere the bracket to a tooth enamel surface.

The present invention further contemplates the application of particles, such as balls, rods, shards, etc., of a chemically activatable material directly to the bracket tooth contact surface 12. In this embodiment, the particles are believed to serve the dual functions of 1) a primary retention surface which has undercut regions to provide mechanical bonding, and 2) chemical bonding with the dental adhesive, and thus will provide enhanced bond strength to the bracket. It should be appreciated that the chemically activatable material applied directly to the bracket tooth contact surface may also be subjected to a chemical activation treatment, such as silanation in the case of $SiO_2$, to even further enhance the bracket bond strength.

COMPARATIVE EXAMPLES

It has been determined that orthodontic brackets made in accordance with the present invention provide significantly improved bond strengths as compared with metal brackets of the type known in the prior art. It has further been determined that the increased bond strengths are obtained without any substantial increase in the risk of removing enamel from the teeth as compared to the bond strengths formed when ceramic brackets are utilized. Since metal brackets are typically more ductile than ceramic brackets, metal brackets may be removed from teeth in a peeling-type action, as opposed to the adhesive fracture-type action required to remove the more rigid ceramic brackets.

Table I below sets forth the results of bond strength tests of prior art metal orthodontic brackets having a woven mesh applied to the tooth contact surface (column 1), compared to orthodontic brackets made in accordance with the present invention (column 2).

TABLE I

| Average Bond Strength | Col. 1 Prior Art Brackets | Col. 2 Brackets made in accordance with the present invention | Col. 3 % Improvement Col. 2 v. Col. 1 |
| --- | --- | --- | --- |
| Shear | 11.9 kg | 20.05 kg | 68% |
| Tensile | 6.7 kg | 11.93 kg | 78% |

The brackets of column 1, which are of a type known in the prior art, are made of stainless steel. A $100 \times 100$ mesh screen, also made of stainless steel, was diffusion bonded to the tooth contact surface of each of the brackets. A dental adhesive sold by 3M under the trade name CONCISE was used to bond the brackets to etched yearling bovine teeth. The adhesive was allowed to properly cure and the bond strength was measured by removing the brackets from the teeth in both shear and tensile modes using an Instron Tensile Testing Machine, set at a cross-head speed of 5 mm/min. The average bond strength in the shear and tensile modes are set forth in column 1.

Column 2 of Table I sets forth the average bond strength, in both the shear and tensile modes, for brackets made in accordance with the present invention. More particularly, stainless steel brackets were provided with a $100 \times 100$ stainless steel mesh diffusion bonded to the tooth contact surface thereof. The brackets were then subjected to argon ion bombardment through a $50 \times 50$ stainless steel screen for a period of 5 minutes at an ion concentration of $1 \times 10^{14}$ ions/cm$^2$. The roughened brackets were then subjected to a silicon dioxide ion bombardment so as to deposit a silicon dioxide coating of about 2 microns thickness in a substantially uniform layer on the exposed surfaces of the tooth contact surface and mesh. The coated tooth contact surface and mesh screen of each bracket was then subjected to treatment with a silane solution as described hereinabove. Thereafter, the orthodontic brackets were secured to etched yearling bovine teeth using the 3M CONCISE brand adhesive. After curing of the dental adhesive, the brackets were removed using the same procedure described above with respect to the brackets of column 1. The results of the bond strength test are set forth in column 2 of Table I.

Column 3 sets forth the percentage improvement, vis-a-vis the prior art-type brackets, of the bond strength of the improved brackets produced in accordance with the present invention. A 68% improvement in shear bond strength was realized and a 78% improvement in tensile bond strength was realized.

While argon ion bombardment was used for roughening the tooth contact surface 12 and mesh 14, it is to be understood that various other high energy ion treatments or other roughening procedures may be used to accomplish this, depending upon the material of the tooth contact surface and mesh 14. Likewise, the size and type of mesh 14 need not be limited to the screen specifically described. Additionally, although silicon dioxide was applied as the chemically activatable material, in layer form, to provide chemical adhesion of the bracket to the dental adhesive. Clearly, other appropriate chemically activatable materials are contemplated for use in the present invention, as described previously.

In addition to improving the mechanical and/or chemical bonding characteristics of a single bracket, the present invention is applicable to provide an overall corrective dental system wherein each of the brackets/appliances has substantially the same bond strength characteristics as the others. For example, in certain orthodontic procedures, metal appliances are adhered to the teeth of a patient and are connected by a common archwire. In order to ensure bond strength uniformity amongst the various orthodontic appliances, the same chemically activatable layer should be applied so that all the appliances have substantially the same overall bond strength characteristics. This allows the clinician to use a single adhesive to bond all the appliances.

The roughening procedure described above can also be used to control the bond strength of individual brackets, to result in a uniform bracket set or system. By controlling the size of the screen through which the ion bombardment is applied, as well as the other previously mentioned parameters, the specific degree of surface area roughening can be controlled. Thus, when greater mechanical bond strength is desired, the mesh size of the screen may be selected to increase the amount of surface area exposed to ion bombardment. Likewise, if less mechanical bond strength is desired, less surface area is exposed. Therefore, by controlling both the chemically activatable layer applied to the brackets and the degree of surface roughening of each bracket, the overall bond strength characteristics of the appliances can be modified to provide a balanced system wherein appliances of different materials or sizes possess substantially uniform bonding characteristics.

Metal brackets having metal mesh screens bonded to the tooth contact surface thereof have been used in the field of orthodontics for some time and provide improvements in terms of bonding characteristics over metal brackets which include no mesh or which include means other than a mesh on the tooth contact surface thereof. One disadvantage of metal brackets with metal mesh, however, is that the bonding strength is based solely on the interlocking mechanical bonding characteristics of the bracket since no chemical bond is formed with the dental adhesive. Bond failure rates for metal brackets with only primary mechanical interlock is typically greater than 10%, which is generally unacceptable. Bond failures require additional time and expense in the overall orthodontic treatment and it is desired to substantially reduce or eliminate such bond failures. It is believed that higher and more predictable bond strengths are obtained by employing the brackets and methods of the present invention and this will result in significantly reduced bond failure rates.

It is to be understood that various other modifications and changes can be made to the present invention as described herein without departing from the scope thereof as defined by the following claims.

What is claimed is:

1. An orthodontic appliance having improved bonding characteristics, comprising:
 a metallic bonding base having a tooth contact surface;
 primary mechanical interlock retention means on said tooth contact surface, said primary retention means including undercut regions which facilitate mechanical bonding of said appliance to a tooth enamel surface using a dental adhesive, said primary retention means selected from the group consisting of (a) particles adhered to said tooth contact surface, (b) a mesh bonded to said tooth contact surface, and (c) undercut regions, including grooves, formed in said tooth contact surface; and
 secondary mechanical bond strength enhancement means applied to said primary retention means and selected from the group consisting of (a) surface etching to increase the surface area of said primary retention means, (b) particles adhered to said primary retention means, and (c) a chemically activatable material deposited on said primary retention means, wherein said secondary mechanical bond strength enhancement means is applied to only a portion of said primary retention means.

2. An orthodontic appliance of claim 1 wherein said primary retention means is a woven mesh diffusion bonded to said tooth contact surface.

3. An orthodontic appliance of claim 1 wherein said secondary mechanical bond strength enhancement means comprises surface etching of said primary retention means to increase the surface area thereof.

4. An orthodontic appliance of claim 3 wherein said surface etching is accomplished by ion bombardment.

5. An orthodontic appliance of claim 1 wherein said secondary mechanical bond strength enhancement means comprises particles having a size in the range of about 1 to 200 microns adhered to said primary retention means.

6. An orthodontic appliance of claim 5 wherein said particles are made of a chemically activatable material.

7. An orthodontic appliance of claim 1 wherein said secondary mechanical bond strength enhancement means comprises a chemically activatable material deposited on said primary retention means.

8. An orthodontic appliance of claim 6 or 7 wherein said chemically activatable material includes an oxide of an element selected from the group of elements consisting of silicon, barium, boron, titanium, magnesium, zirconium, potassium, calcium, sodium and thallium.

9. An orthodontic appliance of claim 8 wherein said chemically activatable material includes silicon dioxide.

10. An orthodontic appliance of claim 6 or 7 wherein said chemically activatable material has been chemically activated.

11. An orthodontic appliance of claim 10 wherein said chemically activatable material has been chemically activated by treatment with silane.

12. An orthodontic appliance of claim 1 wherein said primary mechanical interlock retention means comprises particles of a chemically activatable material adhered to said tooth contact surface.

13. A method of improving the bonding characteristics of an orthodontic appliance having a metallic bonding base with a tooth contact surface, said method comprising the steps of:
 applying primary mechanical interlock retention means on said tooth contact surface of said orthodontic appliance; and
 applying secondary mechanical bond strength enhancement means to said primary retention means, wherein said secondary mechanical bond strength enhancement means application step comprises surface etching of said primary retention means to increase the surface area thereof, said surface etching accomplished by ion bombardment.

14. A method of improving the bonding characteristics of an orthodontic appliance having a metallic bonding base with a tooth contact surface, said method comprising the steps of:
 applying primary mechanical interlock retention means on said tooth contact surface of said orthodontic appliance; and
 applying secondary mechanical bond strength enhancement means to said primary retention mean, wherein said secondary mechanical bond strength enhancement means application step comprises adhering particles having a size in the range of about 1 to 200 microns to said primary retention means, said particles consisting of a chemically activatable material.

15. A method of claim 14 wherein said primary retention means application step comprises bonding a woven metallic mesh to said tooth contact surface and said particles are adhered to said mesh by sintering.

16. A method of claim 15 wherein said sintering is accomplished by plasma spray coating said particles on said mesh.

17. A method of improving the bonding characteristics of an orthodontic appliance having a metallic bonding base with a tooth contact surface, said method comprising the steps of:
 applying primary mechanical interlock retention means on said tooth contact surface of said orthodontic appliance; and
 applying secondary mechanical bond strength enhancement means to said primary retention means wherein said secondary mechanical bond strength enhancement means application step comprises depositing a chemically activatable material on said primary retention means by ion beam implantation.

18. A method of claim 17 wherein said chemically activatable material includes an oxide of an element selected from the group of elements consisting of silicon, barium, boron, titanium, magnesium, zirconium, potassium, calcium, sodium and thallium.

19. A method of claim 18 wherein said chemically activatable material includes silicon dioxide.

20. A method of claim 17 further comprising the step of chemically activating the chemically activatable material.

21. A method of claim 20 wherein said chemical activation step is accomplished by treatment with silane.

* * * * *